US009215790B2

(12) United States Patent
Korenev

(10) Patent No.: US 9,215,790 B2
(45) Date of Patent: Dec. 15, 2015

(54) FORMATION OF MULTIPLE PROTON BEAMS USING PARTICLE ACCELERATOR AND STRIPPER ELEMENTS

(71) Applicant: Siemens Medical Solutions USA, Inc., Malvern, PA (US)

(72) Inventor: Sergey Korenev, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/678,000

(22) Filed: Apr. 3, 2015

(65) Prior Publication Data

US 2015/0305135 A1 Oct. 22, 2015

Related U.S. Application Data

(60) Provisional application No. 61/981,896, filed on Apr. 21, 2014.

(51) Int. Cl.
*A61N 5/00* (2006.01)
*H05H 7/00* (2006.01)
*H05H 7/10* (2006.01)

(52) U.S. Cl.
CPC ................. *H05H 7/001* (2013.01); *H05H 7/10* (2013.01); *H05H 2007/005* (2013.01)

(58) Field of Classification Search
CPC ... H05H 7/001; H05H 7/10; H05H 2007/005; H05H 2007/125
USPC ........................................... 250/492.1–492.3
See application file for complete search history.

(56) References Cited

U.S. PATENT DOCUMENTS 6,462,348 B1 * 10/2002 Gelbart ................. G21K 1/093 250/505.1
7,015,661 B2 3/2006 Korenev

OTHER PUBLICATIONS

J. I. Botman, H. L. Hagedoom, In the Proc. CERN Accelerators School (CAS), 1996 “Cyclotrons, Linacs and Their Applications”, detail paper is “Extraction from cyclotrons”, pp. 169-186.

* cited by examiner

*Primary Examiner* — Michael Maskell
(74) *Attorney, Agent, or Firm* — Peter Kendall

(57) ABSTRACT

A particle acceleration system includes a particle accelerator and at least one beam-transparent stripper element. The particle accelerator is configured to accelerate charged particles along a trajectory. The beam-transparent stripper element(s) is/are positioned along the trajectory. Each beam-transparent stripper element has a surface normal to the trajectory, wherein said surface defines a plurality of apertures configured to cause a first plurality of charged particles that strike the surface to undergo a stripping process while a second plurality of charged particles pass through one or more of the plurality of apertures without undergoing the stripping process.

20 Claims, 8 Drawing Sheets

FORMATION OF MULTIPLE PROTON BEAMS USING PARTICLE ACCELERATOR AND STRIPPER ELEMENTS

CROSS-REFERENCE TO RELATED APPLICATION

This application claims priority under 35 U.S.C. §119(e) from U.S. Provisional Application Ser. No. 61/981,896 filed Apr. 21, 2014, the entirety of which is hereby incorporated by reference herein.

FIELD

Aspects of the present disclosure relate in general to aspects of particle acceleration systems, and more particularly to processing of particle beams in particle acceleration systems.

BACKGROUND

Particle accelerators are used today in various technological fields. As just one example, accelerated particles can be used to generate proton beams for irradiation of targets (e.g., enriched water or other materials) in order to produce medical isotopes. The resulting medical isotopes can be used as biomarkers, e.g., for medical imaging applications such as positron emission tomography (PET).

A collection of charged particles may be referred to as a particle beam. Various types of particle accelerators are used for accelerating particle beams. One type of particle accelerator is a linear accelerator. Another type of particle accelerator is a cyclotron, which is described at, e.g., U.S. Pat. No. 1,948,384 to Lawrence and U.S. Pat. No. 7,015,661 to Korenev, the entire contents of which patents are hereby incorporated by reference herein. A cyclotron accelerates a particle beam (including, e.g., ions such as negatively charged hydrogen ions) by using a rapidly varying electric field. Charged particles that are injected into a vacuum chamber are forced to travel along a spiral trajectory (e.g., with increasing radius for successive orbits) due to a magnetic field, which yields a Lorentz force perpendicular to the direction of motion of the particles. In an isochronous cyclotron, also known as an azimuthal varying field (AVF) cyclotron, the magnetic field strength varies dependent on azimuth of the particle beam along the spiral trajectory. For example, some azimuthal ranges correspond to magnetic hills and others correspond to magnetic valleys. The azimuthal variations in magnetic field strength balance the relativistic mass increase of the particle beam so that a constant frequency of revolution is achieved for the spiral motion.

An accelerated particle beam can be used for nuclear reactions for production of medical isotopes. Nuclear reactions associated with the irradiation of a proton beam upon a target material are often used for generation of medical isotopes such as C-11, N-13, O-15, F-18, Ge-68, Ga-67, Ga-68, Sr-82, Rb-82, Y-86, Tc-99m, I-111, I-123, I-124, Tl-201, or other isotopes. Photonuclear reactions (nuclear reactions resulting from the collision of a photon with an atomic nucleus) may also be used for production of medical isotopes. The production of medical isotopes through nuclear reactions based on target irradiation by a proton beam requires the production of such a proton beam. The standard approach for producing proton beams is to convert negative hydrogen ions into a proton beam and electrons using a stripper foil according to the following process:

$$H^{-} \rightarrow p^{+} + 2e^{-} \quad (1)$$

Process (1) is referred to as a stripping process because electrons are stripped away from the protons. Process (1) may also be referred to as an electron-stripping or proton-stripping process.

Then, the nuclear reaction of protons with O-18 in enriched water yields the medical isotope F-18, for example. The yield of the isotope depends on various factors including beam current, beam kinetic energy, and time of irradiation. It is desirable to produce medical isotopes efficiently.

One approach for increasing the efficiency of isotope production is to adjust particle beam parameters to increase the beam current to yield an increased cross-sectional area for the stripping process, but increasing beam current causes thermal problems for the target. Another approach for increasing efficiency is to increase the number of targets and create multi-beam channels. A traditional implementation for irradiating multiple targets is shown in FIG. 1. Traditional stripper foils 130*a* and 130*b* are placed at different azimuths along an orbit of a spiral trajectory traversed by an accelerated particle beam. FIG. 1 shows a side view of the particle beam's trajectory, which proceeds from left to right in the figure. First, stripper foil 130*a* is encountered. As shown in the FIG. 1, about half the particles in the negative hydrogen ion beam 110 strike stripper foil 130*a* and are thereby converted to protons and electrons according to the process (1). The half of the particles in the negative hydrogen converted to protons and electrons are depicted as the upper half in the view of FIG. 1. As a result of the stripping process, each negative hydrogen ion loses two electrons in stripper foil 130*a* and is converted to a proton. The proton beam resulting from this stripping process is shown as 140*a* in FIG. 1, and the resulting electrons are not shown. The remaining particles in the negative hydrogen ion beam (denoted as 135 in FIG. 1) continue along their spiral trajectory because they did not collide with stripper foil 130*a*, and they subsequently collide with stripper foil 130*b* to yield proton beam 140*b* and electrons (not shown). Thus, two proton beams 140*a*, 140*b* are produced by respective negative hydrogen ion beams 110, 135 and can be used to irradiate respective targets.

The traditional multi-beam approach described regarding FIG. 1 presents several challenges. The position of stripper foil 130*a* (the foil encountered first along the trajectory) has to be carefully fixed in the vertical direction in the view of FIG. 1 to ensure that about half the particles in the incident beam strike stripper foil, so that proton beams 140*a* and 140*b* will have approximately equal yields. Another challenge arises because of the varying diameter (and thus varying cross-sectional area) of a particle beam. FIG. 1 shows stripper foil 130*a* positioned to correspond to the maximum beam diameter (i.e., the beam is widest in the vertical direction of FIG. 1 at the location of stripper foil 130*a*), which improves efficiency, but it is difficult to ensure such a positioning of stripper foil 130*a*. The positioning of stripper foil 130*b* along the vertical and horizontal directions of FIG. 1 does not have to be as tightly controlled as the positioning of stripper foil 130*a*, because stripper foil 130*b* handles all the remaining particles. Still, the precision required regarding positioning of stripper foil 130*a* is difficult to implement and presents practical challenges. Beam cross-sectional variation is difficult to control and predict, in part because magnetic field variation leads to problems of isochronism. FIG. 1 represents an ideal scenario, and often the actual beam dynamics relative to the stripper foil positioning is non-ideal because of imperfections associated with control of varying electric and magnetic fields. Furthermore, with this traditional approach only two stripper foils can be used.

SUMMARY

In some embodiments of the present disclosure, a particle acceleration system includes a particle accelerator and at least one beam-transparent stripper element. The particle accelerator is configured to accelerate charged particles along a trajectory. The beam-transparent stripper element(s) is/are positioned along the trajectory. Each beam-transparent stripper element has a surface normal to the trajectory, wherein said surface defines a plurality of apertures configured to cause a first plurality of charged particles that strike the surface to undergo a stripping process while a second plurality of charged particles pass through one or more of the plurality of apertures without undergoing the stripping process.

In some embodiments, an electron-stripping element for stripping electrons from protons in an ion beam includes a plate having a surface defining a plurality of apertures configured to cause a first plurality of particles of the ion beam that strike the surface to undergo a stripping process while a second plurality of particles of the ion beam pass through one or more of the apertures without undergoing the stripping process, wherein a region of the electron-stripping element surrounding the apertures has a thickness in a range of 1 to 20 microns.

In some embodiments, a method for producing protons comprises providing at least one beam-transparent stripper element to have a surface normal to the trajectory. The surface defines a plurality of apertures therein, wherein each beam-transparent stripper element is configured to cause a first portion of a beam of negative hydrogen ions striking the surface to be converted into protons and electrons while a second portion of the beam passes through one or more of the apertures without being converted into protons and electrons. The method further comprises accelerating the beam of negative hydrogen ions along the trajectory.

BRIEF DESCRIPTION OF THE DRAWINGS

The following will be apparent from elements of the figures, which are provided for illustrative purposes and are not necessarily to scale.

DETAILED DESCRIPTION

This description of the exemplary embodiments is intended to be read in connection with the accompanying drawings, which are to be considered part of the entire written description.

Various embodiments of the present disclosure address the foregoing challenges associated with directing multiple particle beams (e.g., negative hydrogen ion beams) to yield multiple proton beams. Advantageously, with various embodiments the implementation is simpler than traditional approaches and does not depend on extremely precise control of the beam dynamics in order to achieve high efficiency. Additionally, the approach according to various embodiments can be applied to any number of proton beams, unlike the traditional approach shown in FIG. 1 which can only yield two proton beams.

Figure 1:
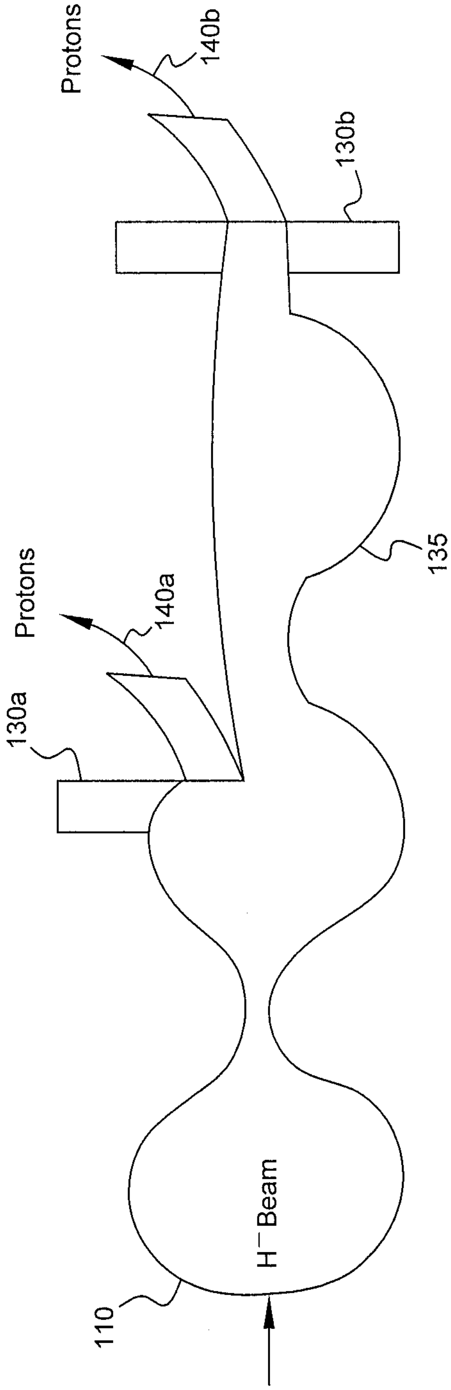
FIG. 1 (Prior Art)
FIG. 1 is an illustration of a traditional approach for forming multiple proton beams in a particle accelerator system.
Figure 2:
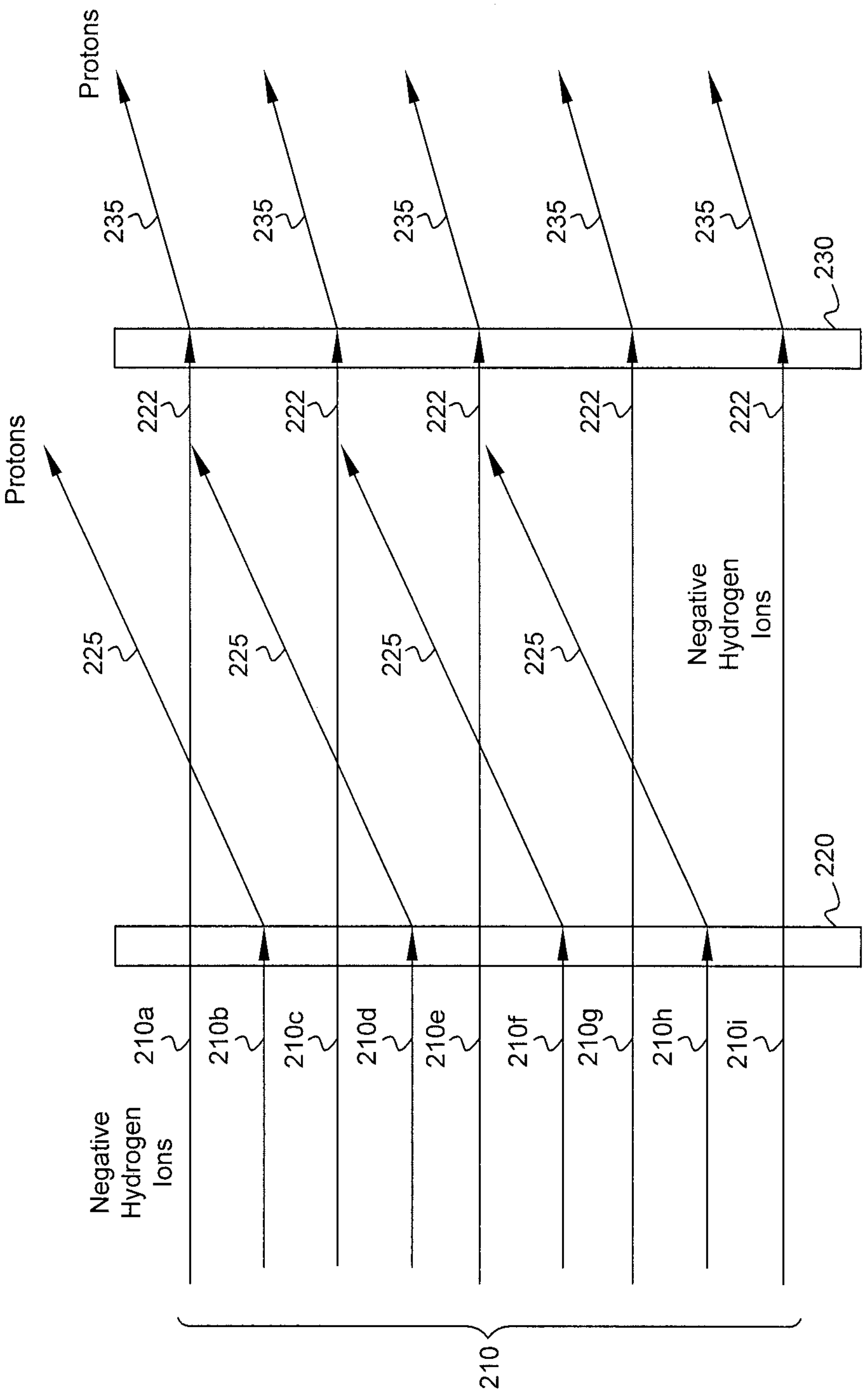
FIG. 2 is an illustration of an improved approach for forming multiple proton beams in accordance with some embodiments.

FIG. 2 shows a negative hydrogen beam 210 and two stripper elements 220, 230 in accordance with some embodiments of the present disclosure. The stripper elements may also be referred to as electron-stripping elements or proton-stripping elements. Similar to FIG. 1, beam 210 proceeds along a trajectory in a left-to-right direction in FIG. 2. First, stripper element 220 is encountered. Stripper element 220, as well as other stripper elements disclosed herein, has a surface typically normal to the trajectory, with a deviation of a few degrees (e.g., 0 to 10 degrees) from 90 being possible. Some portions of the incident beam (denoted as 210*b*, 210*d*, 210*f*, 210*h*) strike stripper element 220 and undergo stripping process (1) to yield protons 225 and electrons (not shown), whereas other portions of the incident beam (denoted as 210*a*, 210*c*, 210*e*, 210*g*, 210*i*) pass through stripper element 220 undisturbed. For convenience, this property of stripper element 220 may be referred to as beam-transparency, and stripper element 220 may be referred to as being beam-transparent because it is transparent to some portions of the incident beam. The undisturbed portions (denoted 222) then strike stripper element 230, which may be a traditional element (such as stripper foils 130*a* or 130*b*) that does not exhibit the property of beam-transparency. Thus, all remaining negative hydrogen ions 222 are converted to protons 235 and electrons (not shown) according to stripping process (1). In this manner, two proton beams 225, 235 are efficiently produced.

Unlike the traditional approach shown in FIG. 1, stripper element 220 does not have to be precisely positioned in the vertical direction of FIG. 2 in order to permit a predetermined proportion (e.g., 50%) of incident negative hydrogen ions to be converted to protons 225 and electrons by stripping process (1). Rather, based on geometrical aspects of the cross-section of stripper element 220 the ratio of ions that pass through stripper element 220 and the ratio of ions that strike stripper element 220 to undergo conversion per stripping process (1) can be controlled. Also, unlike the traditional approach shown in FIG. 1, stripper element 220 does not have to be precisely positioned in the horizontal direction of FIG. 2 to achieve efficient operation. As discussed above, the approach of FIG. 1 depends on precisely positioning stripper foil 130*a* to be struck by only the top half of the incident negative hydrogen ion beam, and that condition can be more easily achieved if the collisions with stripper foil 130*a* occur at a point in the trajectory corresponding to maximum beam diameter. In contrast, the approach in some embodiments as shown in FIG. 2 does not require collisions to occur at maximum beam diameter for efficiency, so the positioning constraint for stripper element 220 is relaxed. Unlike the approach shown in FIG. 1, beam incident upon stripper element 230 is approximately the same size (e.g., in terms of beam width) as the beam incident upon stripper element 220, which simplifies beam processing.

In various embodiments, stripper element 220 has a cross-section that defines a plurality of holes (apertures) through which some fraction of the incident negative hydrogen ion beam can pass. This is referred to as partial beam-transparency. Incident ions that pass through the holes of stripper element 220 undisturbed proceed as beam 222 to stripper element 230, where they are converted to protons 235 and electrons. In contrast, incident ions that strike the surface of stripper element 220 (because they do not arrive at the location of any of the holes) are converted to protons 225 and electrons.

Figure 3:
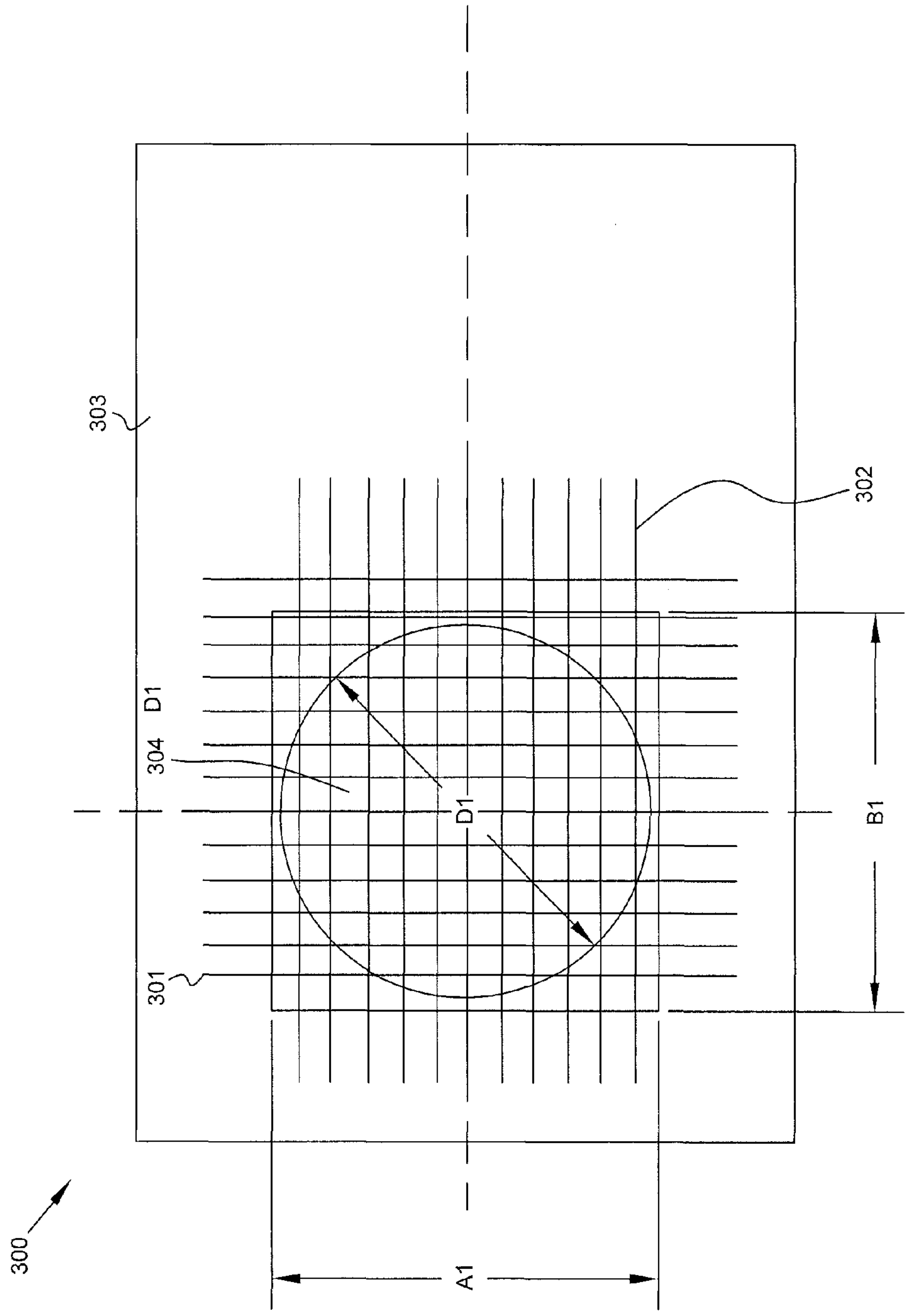
FIG. 3 is a diagram of a beam-transparent stripper element with a grate-like geometry in accordance with some embodiments.

Referring to FIG. 3, in some embodiments, stripper element 300 which can be used to implement stripper element 220 has a matrix (grid) of vertical elements 301 and horizontal elements 302 secured to a holder 303 in a matrix configuration. A stripper element with this grid arrangement may be referred to as a grid-type or grate-type stripper element. Holder 303 may have a thickness in the range of 2-5 mm. Holder 303 defines an aperture, e.g., square-shaped, which is subdivided into respective smaller apertures by the matrix of vertical elements 301 and horizontal elements 302. The vertical elements 301 and horizontal elements 302 may be formed from carbon fibers or carbon nanowires each having a diameter in the range of 1-20 microns in some embodiments. As shown in FIG. 3, the aperture defined by holder 303 may have dimensions A1 and B1 so that incident ion beam 304 (e.g., at its maximum diameter) fits within the aperture. Depending on their spatial position, ions within the beam 304 either pass undisturbed through one of the smaller apertures defined by the matrix of vertical elements 301 and horizontal elements 302, or they strike a vertical element 301 or horizontal element 302 to undergo conversion to protons and electrons according to stripping process (1).

Thus, stripper element 300 is beam-transparent and has a transparency factor that can be controlled by appropriately configuring the vertical elements 301 and horizontal elements 302 to thereby define a particular overall aperture area. For example, the transparency factor $K_{grid\text{-}type}$ for grid-type stripper element 300 can be expressed as:

$$K_{grid\text{-}type}=S_{fibers}/S_{overall\_stripper}*100\% \quad (2)$$

where, $S_{fibers}$ is the area of all the vertical elements 301 and horizontal elements 302 in the plane normal to the incident beam and within the grid shown in FIG. 3, and $S_{overall\_stripper}$ is the area computed as A1*B1 in FIG. 3.

Figure 4:
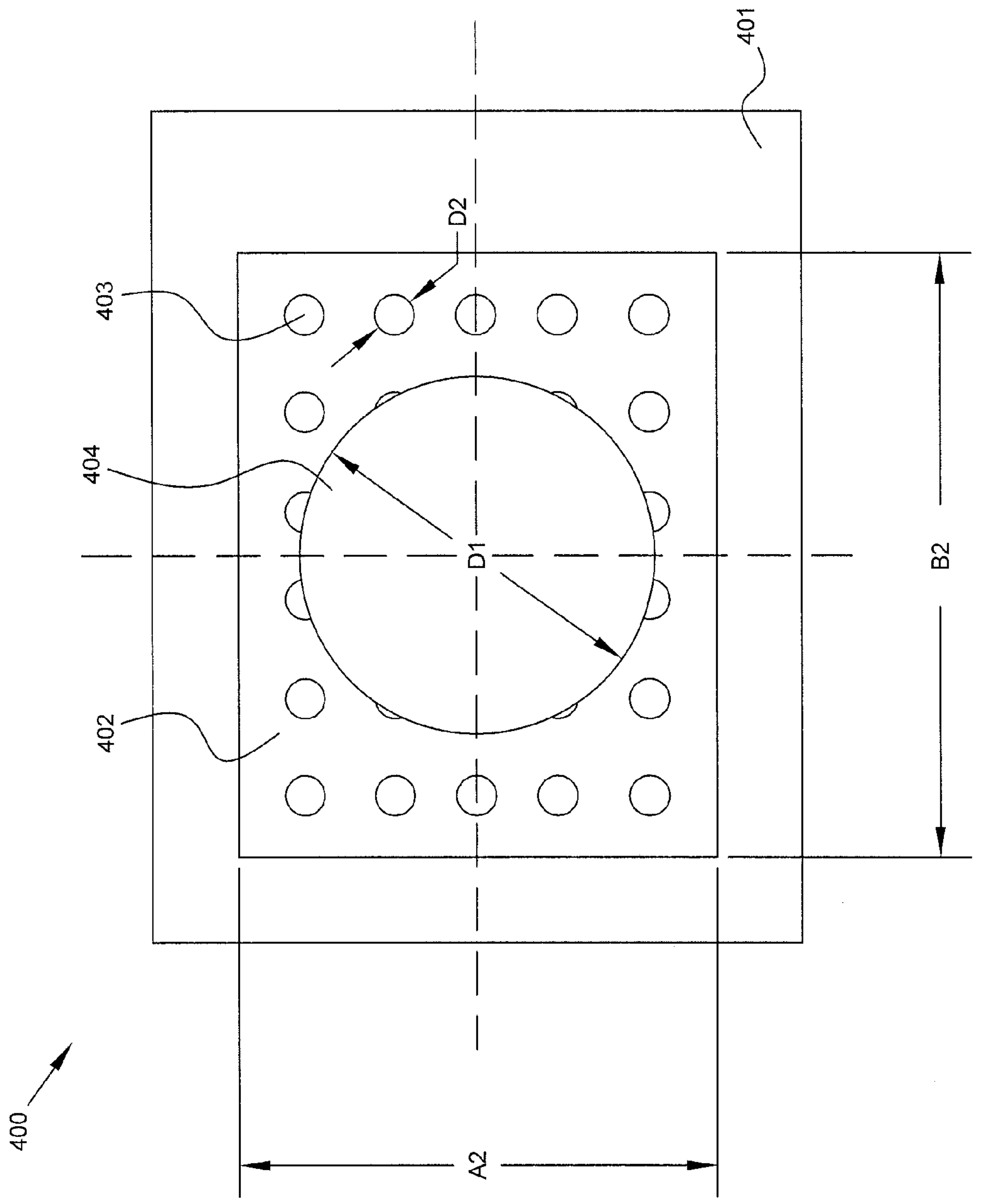
FIG. 4 is a diagram of a beam-transparent stripper element with holes drilled therein in accordance with some embodiments.

Referring to FIG. 4, in some embodiments stripper element 400 which also can be used to implement stripper element 220 includes a holder 401, which may include a sheet of stripper foil from one or more of various carbon materials such as amorphous carbon (AG), polycrystalline graphite (PPG), pyrolitic graphite (PG), graphene, diamond-like carbon (DLC). with a thickness within the range of 1 to 20 microns. Within region 402, which may correspond to the same material as holder 401 or a different material, are defined a plurality of holes 403, which may be circular or elliptical in shape and which may each have a diameter within the range of 0.25 to 1 mm. Region 402 has dimensions A2 and B2 as shown in FIG. 4, e.g., each being in a range of about 10-15 mm. A stripper element with this configuration including holes in a sheet (foil) of material may be referred to as a foil-type stripper element. The holes may be drilled in the foil according to a known drilling process such as laser drilling or other methods for drilling holes, e.g., ion beam drilling, electron beam drilling, electrical spark drilling, etc. In some embodiments, using a different material than graphite for region 402 promotes the drilling of the holes because the graphite alone may be too thin to accommodate drilling of holes. As shown in FIG. 4, when ion beam 404 reaches stripper element 400, some proportion of the ions pass undisturbed through one of the holes 403, and the remaining ions are converted to protons and electrons due to collision with region 402 of stripper element 400 according to stripping process (1).

Thus, stripper element 400 is beam-transparent and has a transparency factor that can be controlled by appropriately configuring the size and quantity of holes to thereby set a particular overall hole area. For example, the transparency factor $K_{foil\text{-}type}$ for foil-type stripper element 400 can be expressed as:

$$K_{foil\text{-}type}=S_{holes}/S_{overall\_stripper}*100\%=N*S_{hole}/S_{overall\_stripper}*100\% \quad (3)$$

where, $S_{holes}$ is the area of all the holes for the stripper element, $S_{hole}$ is the area of an individual hole (assuming the holes are all the same size), N is the number of holes, and $S_{overall\_stripper}$ is the overall area of the stripper element, e.g., area of region 402.

Regardless of whether a grid-type or foil-type stripper element is used, the transparency factor determines the ratio of the beam current on one side of the stripper element to the beam current on the other side. For example, with a foil-type stripper element having transparency factor $K_{foil\text{-}type}$=50%, tests have confirmed that the incoming beam current is about twice the outgoing beam current.

Hence, regardless of whether stripper element 220 is implemented with a geometry as in FIG. 3 or as in FIG. 4, some proportion of incident ions are permitted to pass undisturbed through apertures of the stripper element 220, and the remainder are converted to protons and electrons according to stripping process (1). The proportion of incident ions permitted to pass undisturbed is dependent on the relative overall aperture area compared to overall non-aperture area for the stripper element. In contrast, stripper element 230 is a traditional stripper element and does not have any such apertures, so all incident ions are converted to protons and electrons by stripper element 230. The geometrical configuration of stripper elements 300 (including vertical and horizontal elements 301, 302) and 400 can be varied easily in order to meet design specifications of an overall system, and such variation is easier than varying electric or magnetic fields in a precise manner to achieve the traditional multi-beam approach of FIG. 1.

The activation time (time for nuclear reactions of protons in the stripper element from converted negative hydrogen ions) using grid-type stripper element 300 having vertical elements 301 and horizontal elements 302 is typically a few hours, whereas the activation time using foil-type stripper element 400 is typically a few days. The reason for the difference in activation time is primarily due to the presence of oxygen in the foil-type stripper element and the absence of oxygen in the grid-type stripper element. Because low activation time is desirable when radioactive materials are involved, the use of stripper element 300 may be preferable compared to stripper element 400.

Figure 5:
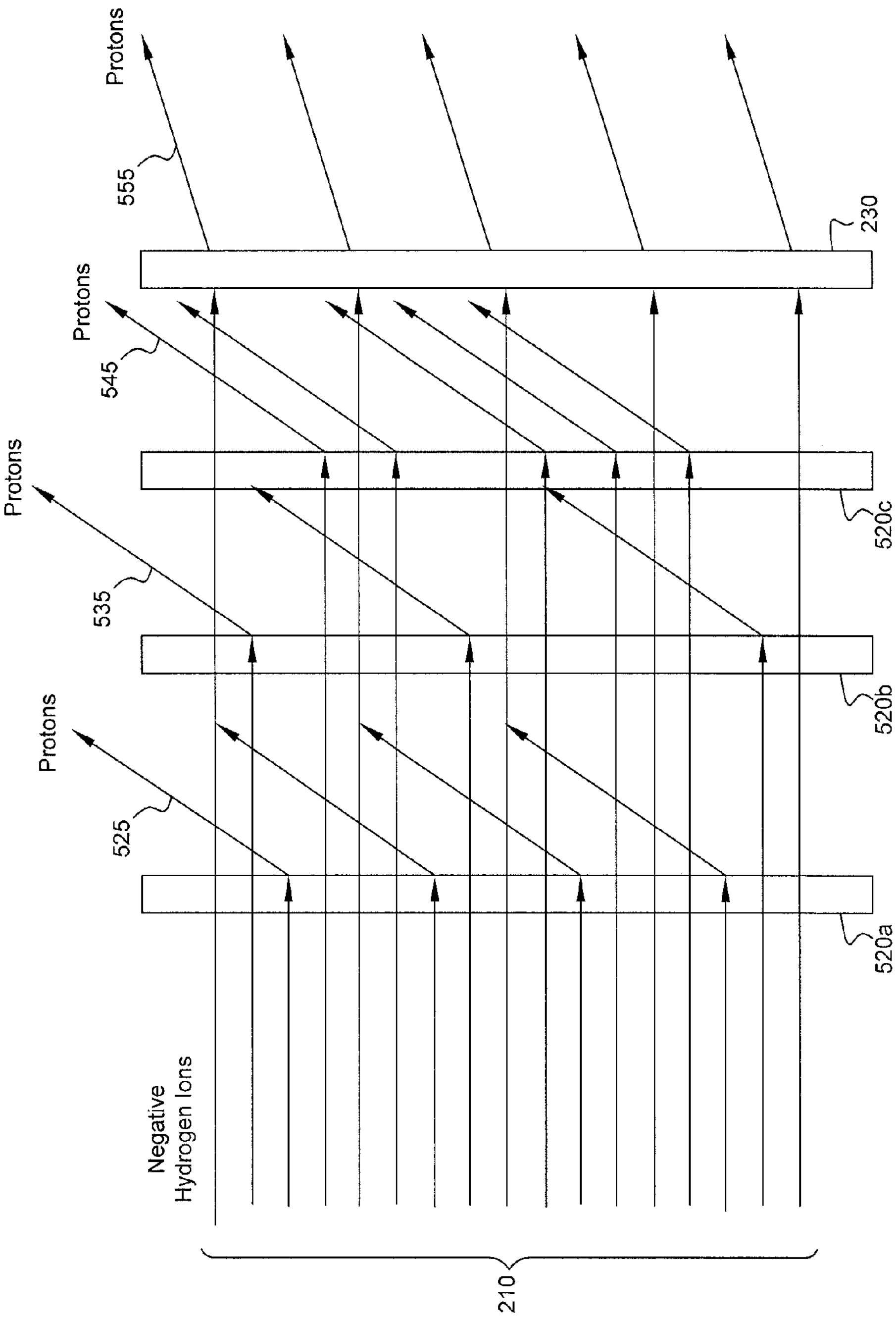
FIG. 5 is an illustration of an approach for forming four proton beams in accordance with some embodiments.

Referring to FIG. 5, more than two proton beams can be generated in accordance with some embodiments. FIG. 5 is similar to FIG. 2 regarding incident negative hydrogen ion beam 210 and stripper element 230 which is not beam-transparent. Three beam-transparent stripper elements 520*a*, 520*b*, 520*c* are configured as shown in FIG. 5 to generate respective proton beams 525, 535, 545 according to stripping process (1). Stripper elements 520*a*, 520*b*, 520*c* may have different beam-transparency characteristics. For example, stripper element 520*a* may allow a higher proportion of incident ions to pass undisturbed through it than does stripper element 520*b*, and 520*b* may allow a higher proportion of incident ions to pass undisturbed through it than does stripper element 520*c*. The final stripper element (stripper element 230) does not allow ions to pass through it undisturbed, instead converting all such ions into protons and electrons.

For each stripper element 520*a*, 520*b*, 520*c*, either a grate-type stripper element 300 or a stripper element 400 with drilled holes may be used. In general, any number of beam-transparent stripper elements may be configured along a particle beam's trajectory in a cyclotron to precede a final stripper element which is not beam-transparent. Each beam-transparent stripper element may be a grate-type stripper element or may have holes drilled in it.

Figure 6:
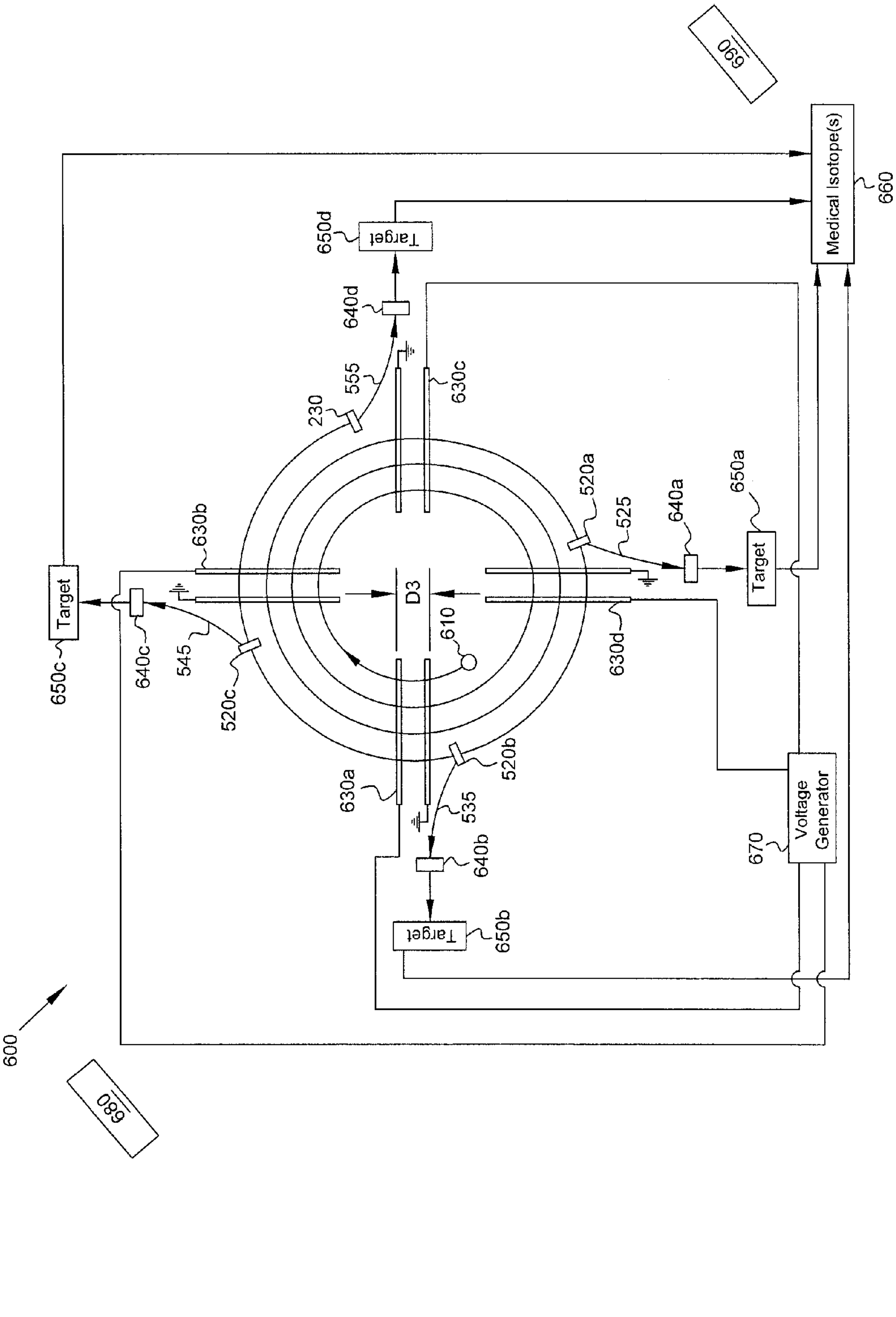
FIG. 6 is a diagram of a system that forms multiple proton beams to irradiate respective targets for generation of medical isotope(s) in accordance with some embodiments using a cyclotron.

FIG. 6 is a diagram of a system in accordance with some embodiments. System 600 includes a cyclotron having at least two accelerator elements. In this example, four accelerator elements 630*a*, 630*b*, 630*c*, 630*d* (collectively 630) are shown, but other numbers of accelerator elements may be used as well. Each accelerator element includes a pair of electrodes separated by a gap. The gap may be the same for each electrode pair, e.g., gap D3 as shown in FIG. 6. One electrode in each pair is grounded, and the other electrode in each pair is coupled to an AC voltage generator 670. System 600 includes at least two magnets that generate a magnetic field normal to the trajectory 620 of accelerated particles. For example, magnet 680 may be in front of the plane of FIG. 6, and magnet 690 may be behind the plane of FIG. 6.

A charged particle injector 610 injects charged particles, e.g., negative hydrogen ions. The particles are accelerated by an electric field applied at the electrodes of each accelerator element. The magnetic field causes the particles to proceed along a roughly circular path, but the magnetic field alters the radius of the roughly circular path so that the trajectory is a spiral.

Stripper elements 520*a*, 520*b*, 520*c* (collectively 520) are beam-transparent and are positioned along the beam trajectory. Each beam-transparent stripper element 520 has a surface that is normal to the trajectory and that defines a plurality of apertures (openings) configured to cause incident negative hydrogen ions that strike the surface to be converted into protons, as shown by 525, 535, 545, respectively, and electrons (not shown). Other incident negative hydrogen ions pass through one or more apertures of the plurality of apertures without undergoing the stripping process. Each stripper element 520 may be a grid-type or foil-type stripper element. Stripper element 230, which is not beam-transparent, causes the remaining negative hydrogen ions to be converted into protons 555 and electrons (not shown). Stripper elements 520*a*, 520*b*, 520*c*, and 230 may be located at magnetic hills (relatively low magnitude regions of the magnetic fields), and the indicated placement of the stripper elements in FIG. 6 is merely illustrative. Output beams systems 640*a*, 640*b*, 640*c*, 640*d* (collectively 640) may include collimators to focus the respective proton beams in order to irradiate respective targets 650*a*, 650*b*, 650*c*, 650*d* (collectively 650). The targets 650*a*, 650*b*, 650*c*, 650*d* may be different from one another and may include substances such as enriched water (e.g., O-18 water). The result of such irradiation may include medical isotope(s) 660, which can be used as biomarkers, e.g., for PET imaging.

Figure 7:
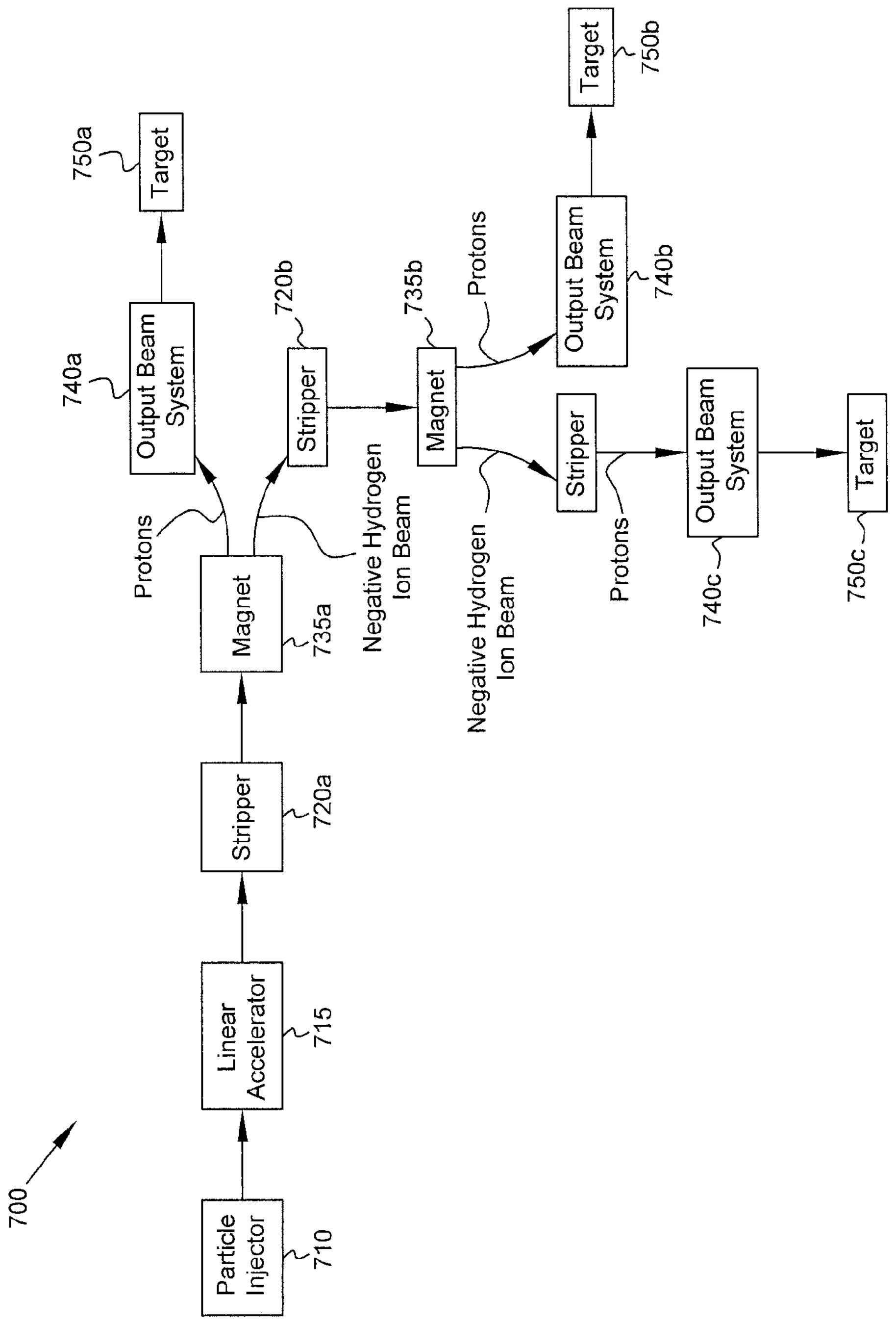
FIG. 7 is a diagram of a system that forms multiple proton beams to irradiate respective targets for generation of medical isotope(s) in accordance with some embodiments using a linear accelerator.

FIG. 7 is a diagram of a system 700 in accordance with some embodiments, using a linear accelerator instead of a cyclotron. A linear accelerator may yield reduced weight (e.g., because no magnet of a cyclotron is needed), reduced cost, and increased beam efficiency relative to a cyclotron. In system 700, a charged particle injector 710 (which may be the same as or different than charged particle injector 610 of FIG. 6) injects charged particles, e.g., negative hydrogen ions, that are accelerated by a linear accelerator 715. The accelerated particle beam encounters beam-transparent stripper element 720*a*, where incident negative hydrogen ions contacting stripper element 720 are converted to protons and electrons. A dipole magnet 735*a* deflects protons to output beam system 740*a*, which includes a collimator for focusing the proton beam to irradiate target 750*a*. Dipole magnet 735*a* deflects negative hydrogen ions in a different direction than the protons, because the negative hydrogen ions have negative electrical charge unlike the protons, which have positive electrical charge. Negative hydrogen ions that passed through apertures in stripper element 720*a* proceed to beam-transparent stripper element 720*b*, where some of the ions are converted to protons and electrons. Each stripper element 720*a*, 720*b* may be a grid-type or foil-type stripper element. A dipole magnet 735*b* deflects resulting protons to an output beam system 740*b*, which focuses protons for irradiating target 750*b*. Dipole magnet 735*b* deflects negative hydrogen ions in a different direction than the protons. The remaining negative hydrogen ions, which passed through apertures in stripper element 720*b*, are converted by stripper 230 into protons and electrons. An output beam system 740*c* focuses protons for irradiating target 750*c*. Although the example configuration shown in FIG. 7 includes two beam-transparent stripper elements, any number of beam-transparent stripper elements may be used.

Figure 8:
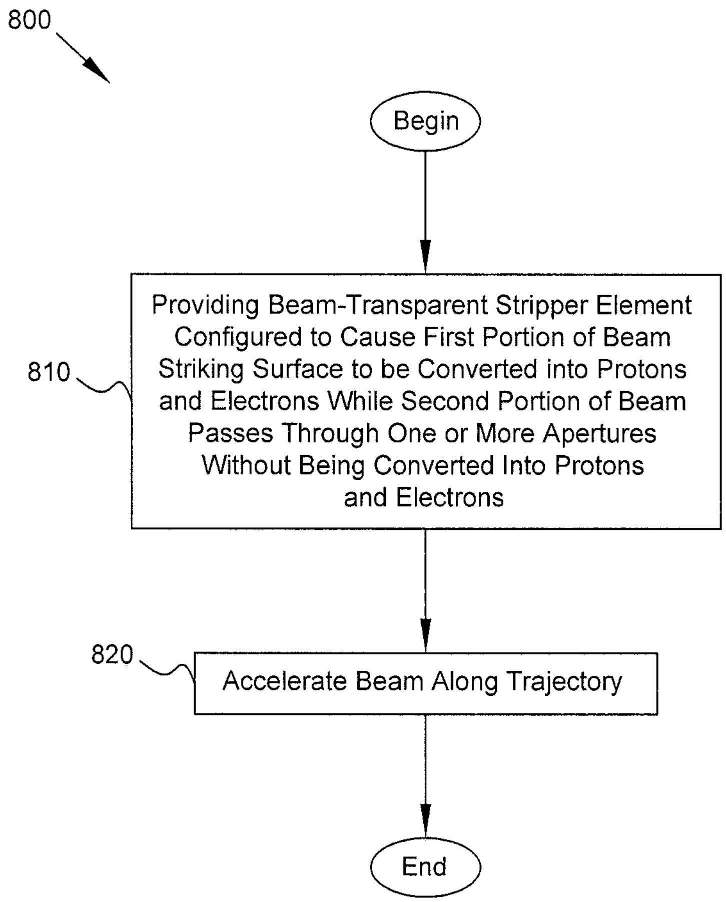
FIG. 8 is a flow diagram of a process in accordance with some embodiments.

FIG. 8 is a flow diagram of a process 800 in accordance with some embodiments. The method includes providing (block 810) at least one beam-transparent stripper element to have a surface normal to the trajectory. The surface defines a plurality of apertures therein, wherein each beam-transparent stripper element is configured to cause a first portion of a beam of negative hydrogen ions striking the surface to be converted into protons and electrons while a second portion of the beam passes through one or more of the apertures without being converted into protons and electrons. The method further comprises accelerating the beam of negative hydrogen ions along the trajectory (block 820).

The use of multiple ion beams in accordance with various embodiments overcomes many problems with prior approaches. As discussed above, stripper element positioning is simplified with various embodiments. Beam dynamics do not have to be as precisely controlled as with prior approaches, and thus magnetic field control and RF frequency control are simplified. The size of the particle beam does not have to be increased in various embodiments, unlike prior approaches for improving efficiency which involved increasing beam size. For example, prior approaches for forming dual ion beams required correction of magnetic field strength and of the RF frequency in order to achieve a configuration as in FIG. 1 wherein about half the ions strike stripper foil 130*a* and the other half strike stripper foil 130*b*. Due to such corrections, the property of isochronism (wherein all ions have equal time of orbit around each loop of the spiral) was violated with prior approaches, but that is not the case with embodiments of the present disclosure. Also, the respective negative hydrogen ion beams in various embodiments can have about the same kinetic energy, which was not possible with the approach of FIG. 1. Additionally, as seen in FIG. 1, the position of the center of beam 110 is different than the position of the center of beam 135. In contrast, in various embodiments, respective ion beams (e.g., beams 210, 222 in FIG. 2) have the same center position, which can make processing easier to control.

Also, referring back to FIG. 2, because the incident ion beams 210, 222 are distributed over a greater contact area of stripper elements 220, 230, thermal load on the stripper elements is decreased (e.g., relative to the approach in FIG. 1), and increased beam current can be used without causing thermal problems. Because of the increased spatial distribution of proton beams 225, 235 compared to proton beams 140*a*, 140*b* in FIG. 1, thermal load on targets irradiated by the proton beams is also reduced. In other words, current density of negative hydrogen ion beams and proton beams is decreased in various embodiments relative to prior approaches, and the decrease in current density advantageously yields dissipation of beam energy in the stripper elements and targets and increases the lifetime of those components, which further increases overall system efficiency. Also, due to decreased beam current density in various embodiments, morphology changes at the surface of stripper foils are reduced or eliminated, yielding a more stable outgoing beam. With more stable beam dynamics, orbit stability is improved and beam output and beam size are advantageously made more homogeneous.

With various embodiments, a given proton beam current can be achieved with a lower ion source (arc) current compared to traditional multi-beam formation approaches. Decreasing the ion source current increases the lifetime of a cathode used in the particle accelerator.

The use of a foil-type stripper or a stripper based on carbon nanomaterials allows beam current across the stripper to be decreased compared to traditional proton generation techniques. The transparency factor has a relatively long lifetime, and a stripper having a drilled foil exhibits few or no changes in surface morphology compared to a traditional stripper foil, increasing the stripper lifetime by a factor of two or more.

Each stripper element in various embodiments (e.g., each beam-transparent stripper element and the stripper element which is not beam-transparent) can be the same size (e.g., same size cross-section). In contrast, with the traditional approach of FIG. 1, stripper foil 130*b* has a larger cross-sectional area than stripper foil 130*a*, because stripper foil 130*b* has to be large enough to accommodate all remaining negative hydrogen ions. By using the same size for each stripper element in various embodiments, cost can be reduced.

Although stripper elements are described above with respect to stripping process (1), in various embodiments similar principles of beam-transparency are applicable to other processes as well. In various embodiments at least one stripper element has a geometry that achieves beam-transparency, such that a first portion of incident particles in the beam strike the surface of the stripper element to undergo a stripping process and a second portion of incident particles in the beam pass through an aperture in the stripper element without undergoing the stripping process.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A particle acceleration system comprising:

a particle accelerator configured to accelerate charged particles along a trajectory; and at least one beam-transparent stripper element positioned along the trajectory and having a surface normal to the trajectory, wherein said surface defines a plurality of apertures configured to cause a first plurality of charged particles that strike the surface to undergo a stripping process while a second plurality of charged particles pass through one or more of the plurality of apertures without undergoing the stripping process.

2. The particle acceleration system of claim 1, further comprising another stripper element that is not beam-transparent and that is positioned along the trajectory, whereby when the particle accelerator is operating and accelerates the charged particles along the trajectory, the second plurality of particles, upon striking the other stripper element, undergo the stripping process.

3. The particle acceleration system of claim 1, comprising at least two beam-transparent stripper elements positioned at different locations along the trajectory.

4. The particle acceleration system of claim 3, wherein the beam-transparent stripper elements include a stripper element having a first plurality of members parallel to one another and a second plurality of members parallel to one another and normal to each of the first plurality of members, the first and second pluralities of members defining the plurality of apertures of said stripper element.

5. The particle acceleration system of claim 3, wherein the beam-transparent stripper elements include a stripper element having a sheet of material with the plurality of apertures defined in said sheet, wherein said apertures are circular or elliptical.

6. The particle acceleration system of claim 3, wherein at least two of the beam-transparent stripper elements are the same size.

7. The particle acceleration system of claim 6, wherein each beam-transparent stripper element includes a portion having a thickness in a range of 1 to 20 microns.

8. The particle acceleration system of claim 1, wherein said at least one beam-transparent stripper element includes a stripper element having a first plurality of members parallel to one another and a second plurality of members parallel to one another and normal to each of the first plurality of members, the first and second pluralities of members defining the plurality of apertures of said stripper element.

9. The particle acceleration system of claim 1, wherein said at least one beam-transparent stripper element includes a stripper element having a sheet of material with the plurality of apertures defined in said sheet, wherein said apertures are circular or elliptical.

10. An electron-stripping element for stripping electrons from protons in an ion beam, said electron-stripping element including a plate having a surface defining a plurality of apertures configured to cause a first plurality of particles of the ion beam that strike the surface to undergo a stripping process while a second plurality of particles of the ion beam pass through one or more of the apertures without undergoing the stripping process, wherein a region of the electron-stripping element surrounding the apertures has a thickness in a range of 1 to 20 microns.

11. The apparatus of claim 10, comprising:

a sheet of material having a first aperture defined therein; and a plurality of members secured to said sheet and spanning said first aperture, said plurality of members subdividing said first aperture into said plurality of apertures.

12. The apparatus of claim 11, wherein said plurality of members includes a first set of members parallel to one another and a second set of members parallel to one another and normal to each of the first set of members.

13. The apparatus of claim 11, wherein said plurality of members include carbon fiber or carbon nanowire members.

14. The apparatus of claim 10, comprising a sheet of material with the plurality of apertures defined in said sheet, wherein said apertures are circular or elliptical.

15. The apparatus of claim 14, wherein said material includes at least one of amorphous carbon (AG), polycrystalline graphite (PPG), pyrolitic graphite (PG), graphene, and diamond-like carbon (DLC).

16. A method of producing protons, the method comprising:

providing at least one beam-transparent stripper element to have a surface normal to the trajectory, said surface defining a plurality of apertures therein, wherein said at least one beam-transparent stripper element is configured to cause a first portion of a beam of negative hydrogen ions striking the surface to be converted into protons and electrons while a second portion of the beam passes through one or more of the apertures without being converted into protons and electrons; and accelerating the beam of negative hydrogen ions along the trajectory.

17. The method of claim 16, further comprising providing another stripper element that is not beam-transparent and that is positioned along the trajectory, whereby when the particle accelerator is operating and accelerates the charged particles along the trajectory, the second portion of the beam, upon striking the other stripper element, is converted into protons and electrons.

18. The method of claim 16, wherein said providing at least one beam-transparent stripper element includes providing two or more beam-transparent stripper elements positioned at different locations along the trajectory.

19. The method of claim 16, wherein said at least one beam-transparent stripper element includes a grate-type stripper element.

20. The method of claim 16, wherein said at least one beam-transparent stripper element includes a foil-type stripper element.

* * * * *